(12) United States Patent
Yamaguchi et al.

(10) Patent No.: US 6,172,003 B1
(45) Date of Patent: Jan. 9, 2001

(54) STRAINS OF DRECHSLERA MONOCERAS AND WEED CONTROL COMPOSITIONS CONTAINING THE SAME

(75) Inventors: Kenichi Yamaguchi; Kazuto Ishihara; Shungo Fukai; Kangetsu Hirase; Takeshi Nakamura; Makoto Nishida, all of Chiba (JP)

(73) Assignee: Mitsui Chemicals, Incorporated (JP)

( * ) Notice: Under 35 U.S.C. 154(b), the term of this patent shall be extended for 0 days.

(21) Appl. No.: 08/958,185

(22) Filed: Oct. 27, 1997

(30) Foreign Application Priority Data

Oct. 31, 1996 (JP) .................................................. 8-290368

(51) Int. Cl.$^7$ .............................. A01N 63/04; C12N 1/14
(52) U.S. Cl. ......................................... 504/117; 435/254.1
(58) Field of Search .......................... 504/117; 435/254.1

(56) References Cited

U.S. PATENT DOCUMENTS

| | | | |
|---|---|---|---|
| 5,424,271 | * 6/1995 | Yamaguchi et al. | 504/117 |
| 5,434,121 | * 7/1995 | Gohbara et al. | 504/117 |
| 5,498,591 | 3/1996 | Gohbara et al. | 504/117 |
| 5,498,592 | 3/1996 | Gohbara et al. | 504/117 |

FOREIGN PATENT DOCUMENTS

| | | |
|---|---|---|
| 0374499 B1 | 2/1994 | (EP) . |
| 0464416 B1 | 9/1994 | (EP) . |
| 3-219883 | 9/1991 | (JP) . |
| 4-226905 | 8/1992 | (JP) . |
| 6-329513 | 11/1994 | (JP) . |
| 7-79784 | 3/1995 | (JP) . |

OTHER PUBLICATIONS

Yabuno, "The Classification and Geographical Distribution of the Genus *Echinochloa*", WeedS Research, vol. 20, pp. 97–104 (1975).

Gohbara et al, "Biological Control Agents for Rice Paddy Weed Management in Japan", Proceedings of International Symposium on Biological Control and Integrated Management of Paddy and Aquatic Weeds in Asia, National Agriculture Research Center, pp. 353–366 (Oct. 1992).

Ellis, Dematiaceous Hyphomycetes, Commonwealth Mycological Institute, Kew, England, pp. 402–452 (1971).

Ellis, More Dematiaceous Hyphomycetes, Commonwealth Mycological Institute, Kew, England, pp. 396–405 (1976).

Williams et al, "DNA polymorphisms amplified by arbitrary primers are useful as genetic markets", *Nucleic Acids Research*, vol. 18, No. 22, 6531–6535 (1990).

* cited by examiner

Primary Examiner—S. Mark Clardy
(74) Attorney, Agent, or Firm—Burns, Doane, Swecker, & Mathis, L.L.P.

(57) ABSTRACT

Cells of a novel strain of *Drechslera monoceras* having practical weed controlling activity against barnyard grass (Echinochloa spp.) at temperatures ranging from 26° C. to 35° C., and exhibiting no pathogenicity to major crops, including rice, are used as a herbicidal component.

18 Claims, 1 Drawing Sheet

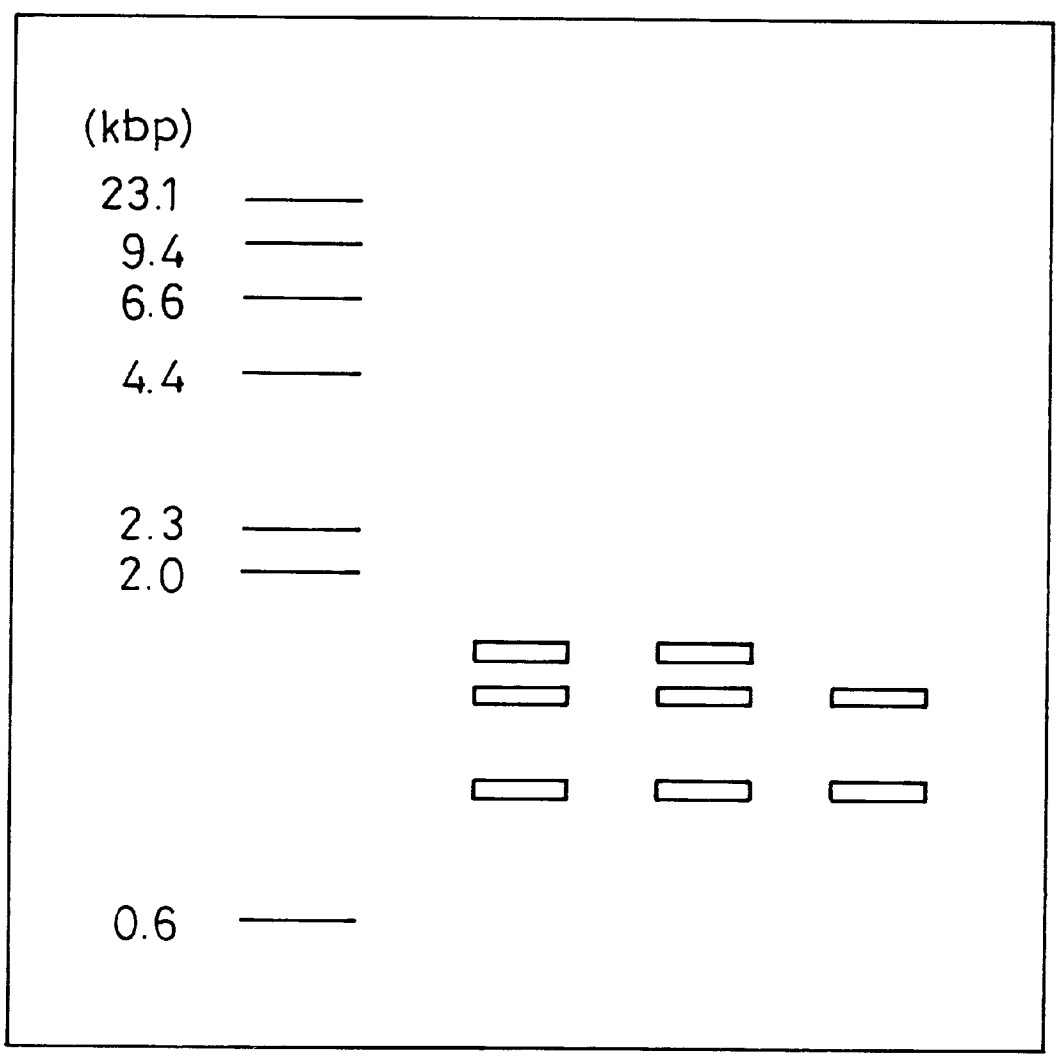

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

CCCAAGGTCC

US 6,172,003 B1

STRAINS OF DRECHSLERA MONOCERAS AND WEED CONTROL COMPOSITIONS CONTAINING THE SAME

BACKGROUND OF THE INVENTION

1. Field of the Invention

The present invention relates to strains of *Drechslera monoceras* having herbicidal activity against barnyard grasses at temperatures ranging from 26° C. to 35° C. and weed control compositions containing the same as an active ingredient.

2. Description of the Related Art

Environmental pollution caused by synthetic agricultural chemicals has become a modern social problem. As a result, new herbicides utilizing natural microorganisms are being touted as a new type of agricultural chemical which will not pollute the environment. For example, DeVine (effective component: *Phytophthora palmivola*) is commercially available in the United States as a weed control composition for strangle vine, a weed of family Asclepiadaceae, and Collego (effective component: *Colletotrichum gloeosporioides*), BioMal (effective component: *Colletotrichum gloeosporioides* f.sp. *malvae*) and LuboaII (effective component: *Colletotrichum gloeosporioides* f. sp. *cuscutae*) are commercially available as a weed control agent for northern jointvetch, a leguminous weed, in the United States, Canada and China, respectively.

No herbicides, that utilize living cells, are currently registered as agricultural chemicals in Japan. However, research is being done on the effect of mycoherbicides on weeds in rice paddies or lawns (Integrated Management of Paddy and Aquatic Weeds in Asia. FFTC Book Series No. 45, 1994). In particular, intensive research on mycoherbicides for barnyard grasses, which is a troublesome weed in rice cultivation, is being performed and it is reported in Japanese Patent Laid-open No. 1991/219883 (kokai 3-219883), Japanese Patent Laid-open No. 1994/329513 (kokai 6-329513) and others that a strain of genus Drechslera, which is a plant pathogen, is effective for controlling weeds of genus Echinochloa. However, such research has not reached the stage of practical applications.

Wild species of barnyard grasses are known as weeds in rice cultivation regions of the world, particularly in Japan, where they have long been regarded as troublesome weeds. According to Yabuno (Zasso Kenkyu (Weeds Research), volume 2, 1975), six species of wild barnyard grasses are known in the world, i.e., *Echinochloa oryzicola*, *E. colona*, *E. pyramidalis*, *E. stagnina*, *E. haploclada* and *E. crus-galli*. This latter species is further divided into three varieties, i.e., *E. crus-galli* var. *formosensis*, *E. crus-galli* var. *crus-galli* and *E. crus-galli* var. *pratycola*. Barnyard grasses known as troublesome weeds in rice cultivation are considered to be those produced by the natural crossing of plants between different species or subspecies of genus Echinochloa. A mycoherbicide to control barnyard grasses must have herbicidal activity against plants of all species and subspecies of genus Echinochloa, but must have no pathogenicity in major crops including rice. Further, weeds of genus Echinochloa start to germinate at 10° C. and grow vigorously over a broad range of temperatures ranging from 15° C. to 35° C. Therefore, a mycoherbicide to control barnyard grasses should preferably have selective herbicidal activity against weeds of genus Echinochloa over a broad range of temperatures from a low of about 15° C. to a high of about 35° C.

Strains of mold fungi isolated from plants of genus Echinochloa, *Drechslera monoceras* IFO-9619 and IFO-9800, are stored at the Institute for Fermentation in Osaka. However, as explained below, these strains have no herbicidal activity against barnyard grasses known as troublesome weeds in rice cultivation.

Strains of *Drechslera monoceras* having herbicidal activity against barnyard grasses, such as MH-9011 (FERM BP-3416) are described in Japanese Patent Laid-open No. 1992/226905. However, as explained below, these strains have herbicidal activity against barnyard grasses at normal temperatures, i.e., about 25° C., but almost no activity at temperatures above 30° C.

The reality is that many species other than barnyard grasses grow in rice paddies and croplands, and these weeds also have to be controlled in rice cultivation. The general practice today is to apply several herbicides effective on different weeds in combination or as a composition of mixture of a multiple number of herbicides. As a result, the use of synthetic agricultural chemicals has increased considerably. Application of large amounts of synthetic agricultural chemicals is creating not only concerns about pollution of the water, soil or the like, but is creating a vicious circle of inducing chemically-resistant weeds and insect pests or pathogens having drug resistance. Thus, there is an urgent need to develop new agricultural chemicals that are safe to humans and animals but do not pollute the environment. At the same time, enforceable measurements to reduce the use of synthesized agriculture chemicals are required.

SUMMARY OF THE INVENTION

The problem that the present invention attempts to solve is the elimination of the disadvantages of the conventional weed controlling method in which only synthetic agricultural chemicals are used by providing a mycoherbicide that is harmless to humans and animals and does not cause environmental pollution. Accordingly, an objective of the present invention is to provide new strains of *Drechslera monoceras* having selective herbicidal activity against barnyard grasses troublesome in rice cultivation at a range of temperatures in which said grasses grow vigorously, and to provide a weed control composition containing living cells of said strains as an effective component.

A further objective of the present invention is to provide a weed controlling method which would reduce the use of synthetic agricultural chemicals so as to curtail their impact on the environment by using said cells and existing chemical herbicides in combination.

In order to solve the abovementioned problems, the present inventors searched among various plant pathogens existing in nature and isolated a new strain of *D. monoceras* having practical herbicidal activity against barnyard grasses at a range of temperatures in which said weeds grow vigorously, but having no pathogenicity in major crops, including rice, thereby the present invention has been accomplished.

Thus, the present invention comprises strains of *D. monoceras* having a selective herbicidal activity against barnyard grasses (Echinochloa spp.) at temperatures ranging from 26° C. to 35° C., and a weed control composition containing said *D. monoceras* cells as an effective ingredient.

Strains of *D. monoceras* according to the present invention have herbicidal activity against all species of barnyard grass weeds (Echinochloa spp.) at temperatures ranging from 26° C. to 35° C., as well as normal temperatures, and exhibit a practical weed controlling effect. On the other hand, they have no pathogenicity in major crops, including rice, and they exhibit a high selectivity which is considered to be difficult to attain in chemical herbicides.

Furthermore, the combined application of cells of strains of *D. monoceras* according to the present invention plus a chemical herbicide or a mixed composition of the two can reduce the amount of chemicals necessary to control barnyard grasses, thus helping to eliminate the recent phenomena of environmental pollution and an increased incidence of chemically-resistant weeds.

BRIEF DESCRIPTION OF THE DRAWINGS

FIG. 1 shows electrophoresis patterns of PCR products.

DETAILED DESCRIPTION OF THE INVENTION AND PREFERRED EMBODIMENTS

The strains of *D. monoceras* according to the present invention are plant pathogens selected from tens of thousands of different microorganisms living in nature by a selective herbicidal activity test using weeds of genus Echinochloa and rice plants (selected for non-pathogenicity to beneficial crops such as rice). These strains exhibit practical herbicidal activity against barnyard grasses at temperatures above 30° C. as well as at normal temperatures of around 25° C., namely at temperatures ranging from 26° C. to 35° C.

Barnyard grasses to be controlled are weeds classified as Echinochloa spp., such as *E. oryzicola, E. crus-galli* var. *formosensis* and *E. crus-galli* var. *crus-galli*. The strains of *D. monoceras* according to the present invention have no pathogenicity on major crops, such as rice, barley, rye, wheat and oat, and grasses such as orchard grass, Italian rye grass and perennial rye grass.

The strains of the present invention are characterized in that said strains have herbicidal activity against barnyard grasses at temperatures ranging from 26° C. to 35° C., and have two nucleotide sequences that hybridize with the DNA having a sequence of SEQ ID NO: 1 existing at a distance between 1.5 kbp and 1.6 kbp on a chromosome.

Examples of representative strains of *D. monoceras* according to the present invention include MH-1901 (FERM BP-6091) and MH-2001 (FERM BP-6092). These strains are deposited with the abovementioned access numbers at the National Institute of Bioscience and Human-Technology Agency of Industrial Science and Technology, Ministry of International Trade and Industry, 1-3 Higashi 1-Chome, Tsukuba-shi, Ibaraki Prefecture, Japan dated Oct. 30, 1996 according to the Budapest Treaty on the International Recognition of the Deposit of Microorganisms for the Purpose of Patent Procedure.

The strains of *D. monoceras* according to the present invention can be used in weed control compositions as cultured living cells, cell culture filtrate or as mixture of cells and filtrate. Furthermore, hyphae or conidia or mycelia containing both hyphae and conidia can be used as the living cells.

Mold fungi belonging to genus Drechslera can be produced on a large scale by an established method as disclosed in Japanese Patent Laid-open 1995/79784 (kokai 7-79784), and thus are available for industrial use as a weed control composition.

Weed control compositions using cells of *D. monoceras* according to the present invention can be obtained using said cells in their pure form. However, it is generally preferable to obtain them as formulas, such as granules, powders, wettable powders, flowable agents, emulsions, liquids and the like, by mixing the living cells having persistency, such as conidia, with inactive carriers.

There are no particular restrictions on the carrier, and either solid or liquid carriers customarily used for agricultural and horticultural formulations can be used as long as they are biologically inactive. Examples of solid carriers include minerals such as clay, talc, kaolin, bentonite, white carbon, zeolite, silica and diatomaceus earth, vegetative materials such as corn powder, soybean powder or starch and polymers such as polyvinyl alcohol and polyalkyls. Examples of liquid carriers include various organic solvents such as decane and dodecane, vegetable oils, mineral oils and water.

As to auxiliary agents, surfactants, binders and stabilizers such as antioxidants and pH controlling agents can be used as required.

The appropriate number of *D. monoceras* cells to be used in a weed control composition according to the present invention varies depending on the form of the formulations and the method of application. In general, the number in application to a field ranges from $1 \times 10^6$ to $1 \times 10^{12}$, preferably from $1 \times 10^8$ to $1 \times 10^{10}$ conidia per are.

An adequate weed control effect can be also further enhanced by combining the weed control composition of *D. monoceras* according to the present invention with a chemical herbicide in a small amount which is otherwise insufficient if used alone in such small amount, i. e., the amount of the chemical herbicide can be effectively reduced. Therefore, said cells contribute not only to crop production but also to curtailing environmental pollution by reducing the use of chemical herbicides.

If the weed control composition of *D. monoceras* cells of the present invention is used in combination with synthetic agricultural chemicals designated for barnyard grasses, such as diphenyl ether herbicides, amide herbicides and carbamate herbicides, a synergistic effect is achieved to enhance the herbicidal activities of both compositions. Also, the efficacy of the weed control composition of the present invention can be extended to broadleaf weeds by mixing it with chemical herbicides designated for said weeds, such as diazine herbicides, sulfonylurea herbicides and triazine herbicides. In this case, the dosage of *D. monoceras* cells is also reduced.

The possible mechanism for this synergistic action is that infection by *D. monoceras* according to the present invention damages the plant tissues to enable greater absorption and mobilization of the chemical herbicides. Similarly, the chemical herbicides also damage the plant tissues to promote the infection and growth of *D. monoceras*, thereby fortifying the herbicidal activity of both compositions.

Examples of the chemical herbicides include 2,4-D, MCPB, phenothiol, naproanilide, propanil, ethobenzanide, buromobutide, mefenacet, butachlor, metolachlor, pretilachlor, thenylchlor, diflufenican, thiobencarb, molinate, dimepiperate, esprocarb, pyributicarb, karbutilate, asulam, diuron, linuron, dymron, cumyluron, bensulfuron-methyl, pyrazosulfuron-ethyl, cinosulfuron, imazosulfuron, azimsulfron, cyclosulfamuron, butamifos, piperophos, anilofos, trifluralin, pendimethalin, quinoclamine, quinchlorac, dichlobenil, ioxynil, sethoxydim, sulcotrione, befenox, acifluorphene-sodium, fluazifop-butyl, quizalofop-ethyl, cyhalofop-butyl, benfuresate, cinmethylin, norflurazon, isoxaflutole, bentazone, bromacil, pyrazolate, pyrazoxyfen, benzofenap, imazapyr, imazaquin, cafenstrole, pentoxazone, pyriminobac-methyl, bispyribac-sodium, simazine, atrazine, simetryn, prometryn, dimethametryn.

A weed control composition of *D. monoceras* cells according to the present invention can be used in combination with a known chemical herbicide by applying the two separately, but can be used in a form of a mixed composition in the case of chemical herbicides having no inhibiting activity on conidium germination or mycelium extension of said cells, such as mefenacet and naproanilide. The number of *D. monoceras* cells in a weed control composition according to the present invention varies depending on the form of the formulation. However, the number generally ranges from $1\times10^5$ to $10^8$, preferably from $1\times10^6$ to $1\times10^7$ per gram in solid formulations such as granules and wettable powders.

*D. monoceras* according to the present invention and a weed control composition containing the same as an effective component will be explained in more detail by the following Examples. However, it is to be understood that the invention is not intended to be limited to the Examples.

EXAMPLE 1

Isolation of *D. monoceras* of the Present Invention

Naturally diseased barnyard grasses were harvested and pathogens were isolated from morbid tissues of leaf blades and vaginas. More specifically, 1 cm squire tissue sections with a lesion in the center were cut. The sections were soaked in a 70% aqueous ethyl alcohol solution for 1 to 2 seconds, then in an aqueous sodium hypochlorite solution having an effective chlorine concentration of about 2% for 10 minutes to pasteurize the surface of the sections. The morbid tissue sections thus pasteurized were washed with sterile water three times, placed on an agar medium supplemented with antibiotics and then incubated statically in an incubator. Tips of growing mycelia were picked up under a stereoscopic microscope and transferred to a nutrient medium to carry out pure culture.

Test Example 1

Verification of Selective Herbicidal Activity and Identification of Isolated Mold Fungi (1) Verification of selective herbicidal activity Different species of weeds of genus Echinochloa and rice plants were grown in test tubes under sterile conditions to prepare test materials. Specifically, seeds of weeds of genus Echinochloa, i.e., *E. oryzicola, E. crus-galli* var. *formosensis* and *E. crus-galli* var. *crus-galli*, and rice plants, i.e., Nipponbare, Koshihikari and Sasanishiki, were pasteurized in the same manner as described above and seeded and grown in test tubes for plants with sterile distilled water.

On the other hand, purely isolated mold fungi were cultured on a plate with potato-dextrose agar medium (Difco) at 25° C. for 1 week and then the outer edge of the resultant colonies were stamped out using a cork borer to obtain mecerial discs for inoculation.

The mecerial discs were inoculated into the test tubes in which weeds of genus Echinochloa or rice plants had grown and then incubated in a chamber for plant growth. Two weeks after inoculation, the effect of the test fungi on weeds of genus Echinochloa and rice plants was evaluated into 4 grades, i.e., −(no effect), +, ++ and +++ (withering). Results are shown in Table 1-1 and Table 1-2.

TABLE 1-1

Herbicidal activity of mold fungi according to the present invention on weeds of genus Echinochloa

| Strain | *E. oryzicdia* | *E. crus-galli* var. *formosensis* | *E. crus-galli* var. *crus-galli* |
| --- | --- | --- | --- |
| IFO-9619* | − | − | − |
| IFO-9800* | − | − | − |
| MH-9011* | + | ++ | ++ |
| MH-1901 | +++ | +++ | +++ |
| MH-2001 | +++ | +++ | +++ |
| None | − | − | − |

*Known strain.

TABLE 1-2

Pathogenicity of mold fungi according to the present invention to rice plants

| Strain | Nipponbare | Koshihikari | Sasanishiki |
| --- | --- | --- | --- |
| IFO-9619* | − | − | − |
| IFO-9800* | − | − | − |
| MH-9011* | − | − | − |
| MH-1901 | − | − | − |
| MH-2001 | − | − | − |
| None | − | − | − |

*Known strain.

(2) Identification of Mold Fungi

Mold fungi having a marked herbicidal effect on weeds of genus Echinochloa and having no effect on rice plants were identified. MH-1901 and MH-2001 exhibited grayish black colonies and irregular growth on a malt agar medium (Difco). The conidia had distinctive hila measuring 87.5–127.5 $\mu$m×15–17.5 $\mu$m and a slightly curved shape. In the main, there were 5 to 7 septa and a maximum of 9. Conidiophores were straight. From these characteristics, both mold fungi MH-1901 and MH-2001 were identified as *Drechslera monoceras*, according to the classification of Ellis (Ellis, M. B., 1971: Demariaceus Hyphomycetes. Commonwealth Mycological Institute, Kew, England and Ellis, M. B., 1976: More Demariaceus Hyphomycetes. Commonwealth Mycological Institute, Kew, England). These novel strains, MH-1901 and MH-2001, were deposited with access numbers FERM BP-6091 and FERM BP-6092 respectively, at the National Institute of Bioscience and Human-Technology Agency of Industrial Science and Technology as described above.

Test Example 2

Distinction of *D. monoceras* Strains According to the Present Invention and Known Strains The strains of *D. monoceras* MH-1901 and MH-2001 according to the present invention and a known strain of *D. monoceras* MH-9011 (deposited with access number FERM BP-3416 at the National Institute of Bioscience and Human-Technology Agency of Industrial Science and Technology according to the Budapest Treaty on the international recognition of the deposit of microorganisms for the purpose of patent procedure) were compared using electrophoresis patterns of PCR products obtained by the RAPD method (Random Amplified Polymorphic DNA, Williams, J. G. K. et al (1990); DNA polymorphisms amplified by arbitrary primers are useful as genetic markers, Nucl. Acids Res., Vol. 18).

DNAs were extracted and purified from cells of MH-1901, MH-2001 and MH-9011 according to the customary method. The purified DNAs and a commercially available PCR reagent (Takara Shuzo Co., Ltd.) were mixed in a ratio shown in Table 2 to prepare PCR reaction solutions.

TABLE 2

Composition of PCR reaction solution

| | |
|---|---|
| PCR buffer (×10) | 1.5 μl |
| 25 mM magnesium chloride | 0.3 μl |
| 2.5 mM dNTP | 0.6 μl |
| Taq polymerase | 0.06 μl |
| 0.1 μM primer | 0.6 μl |
| DNA (1 ng/μl) | 0.5 μl |
| Sterile water | 11.34 μl |

OPE-1 for RAPD (5'-CCCAAGGTCC-3' (SEQ ID NO:1), a product of Operon Technology) was used as the primer. The PCR reaction was performed using a DNA thermal cycler (Gene Amp PCR System 9600, a product of The Perkin Elmer Co.) starting with one cycle for 2 minutes at 94° C. followed by 45 cycles as follows: 10 seconds at 94° C., 1 minute at 40° C. and 1 minute at 72° C., then finishing for 10 minutes at 72° C.

DNAs obtained by the PCR reaction were subjected to submarine electrophoresis on 1.5% agarose gel (50 V for 50 minutes), the gels were soaked for 20 minutes in an aqueous ethidium bromide solution (0.5 μm/ml) for staining, then the band patterns of PCR products were examined under ultraviolet radiation. Results are shown in FIG. 1.

Comparison of electrophoresis patterns of the PCR products showed that MH-1901 and MH-2001 according to the present invention were evidently different from MH-9011.

Test Example 3

Herbicidal Activity of *D. monoceras* According to the Present Invention at Different Temperatures Cells of *D. monoceras* MH-1901 and MH-2001 according to the present invention and a known strain MH-9011 were each inoculated on an oatmeal agar medium (Difco) and incubated statically at 25° C. for 2 weeks. Conidia formed on the surface of colonies were suspended in a 0.02% aqueous Triton X-100 (Rohm & Haas Co.) solution to formulate a weed control composition having *D. monoceras* cells (1×10$^5$ conidia/ml) as an effective component.

On the other hand, 1/10000-are pots were filled with rice paddy soil, seeded with 50 seeds per pot of barnyard grass, then the plants were grown to the one-leaf stage. The pots with the plants were filled with water to a depth of about 5 cm. To these pots, 1 ml each of the abovementioned weed control composition was added dropwise. The pots were placed in a weather controlled room (illumination: 10,000 luxes, light/dark: 12/12 hours) set at temperatures of 10, 20, 25, 30° C. and 40° C. to cultivate the barnyard grass. Two weeks after the treatment with the weed control compositions, the numbers of surviving plants and withered plants were counted to calculate ratios of controlling barnyard grass. The tests were triplicated. Average controlling ratios are shown in Table 3.

TABLE 3

Herbicidal activity of *D. monoceras* according to the present invention at different temperatures

| Temperature (° C.) | 10 | 20 | 25 | 26 | 28 | 30 | 35 | 40 |
|---|---|---|---|---|---|---|---|---|
| MH-9011* | –** | 76 | 98 | 90 | 70 | 4 | 2 | –*** |
| MH-1901 | –** | 100 | 100 | 100 | 100 | 100 | 70 | –*** |
| MH-2001 | –** | 100 | 100 | 100 | 100 | 100 | 70 | –*** |
| No inoculation | –** | 0 | 0 | 0 | 0 | 0 | 0 | –*** |

*: Known strain.
**: Barnyard grass did not grow due to the low temperature.
***: Most barnyard grass withered due to the high temperature.

Formulation Example 1

Wettable Powder

A suspension containing conidia of *D. monoceras* MH-1901 (1×10$^9$) and 90 g of TOALITE (Toa Kasei Co., Ltd.) as diatomaceous earth were throughly mixed, the admixture was thoroughly dried in air at room temperature and the dried material was crushed. The resultant crushed material was mixed and kneaded with Newkalgen (Takemoto Oil & Fat Co., Ltd.) as a surface active agent and the mixture was passed through a screen to obtain a wettable powder of *D. monoceras* of the present invention.

Formulation Example 2

Powder

A suspension containing conidia of *D. monoceras* MH-2001 (1×10$^9$) and 90 g of TOALITE (Toa Kasei Co., Ltd.) were throughly mixed, then the admixture was thoroughly dried in air at room temperature. The dried material was crushed, then passed through a screen to obtain a powder of *D. monoceras* of the present invention.

Formulation Example 3

Granule

A suspension containing conidia of *D. monoceras* MH-1901 (1×10$^9$), 88 g of TOALITE and 2 g of Cellogen (Daiichi Kogyo Seiyaku Co., Ltd.) as sodium carboxymethylcellulose were throughly mixed, then the admixture was granulated using asmall-sized extrusion granulator. The granulated material was passed through a screen, then dried in air to obtain granules of *D. monoceras* of the present invention.

Formulation Example 4

Granule Mixed with Chemical Herbicide

10% by weight of finely crushed granules of EMUON (containing 18.1% CNP as an effective component; a product of Sankyo) and 78 g of zeolite (Sanyo-Kokusaku Pulp Co., Ltd.) were throughly mixed, then a suspension containing conidia of *D. monoceras* (1×10$^8$) was added to moisten the resultant mixture. 2 g of Cellogen (Daiichi Kogyo Seiyaku Co., Ltd.) were added, the admixture was thoroughly mixed, then granulated using a small-sized extrusion granulator. The granulated material was passed through a screen and dried in air to obtain granules of *D. monoceras* of the present invention mixed with CNP.

Test Example 4

Application Test in Combination of *D. monoceras* According to the Present Invention and Chemical Herbicide for Barnyard Grass 1/1000-are quantitative pots were filled with rice paddy soil, seeded with about 100 seeds per pot of barnyard grass, then the plants were grown to the one-leaf stage. The pots were filled with water to a depth of about 5 cm. The plants were treated with the wettable powder prepared according to Formulation Example 1 along with a chemical herbicide for barnyard grass, namely, HINOCHLOA granules (effective component: mefenacet). The pots were placed in a weather controlled room (illumination: 10,000 luxes, light/dark: 12/12 hours) set at a temperature of 30° C. to cultivate the barnyard grass. One month after the treatment, the numbers of surviving plants were counted to calculate ratios of controlling barnyard grass using the formula below. The tests were triplicated. Average controlling ratios are shown in Table 4. Controlling ratio (%)=[(Number of surviving plants in non-treated group−Number of surviving plants in treated group)/(Number of surviving plants in non-treated group)]×100

TABLE 4

Herbicidal effect of application in combination of
D. monoceras according to the present invention and chemical
herbicide for barnyard grass (average controlling ratio, %)

| Number of conidia | HINOCHLOA granules (mg) | | | | |
|---|---|---|---|---|---|
| | 300 | 100 | 30 | 10 | 0 |
| $1 \times 10^6$ | 100 | 100 | 100 | 100 | 100 |
| $3 \times 10^5$ | 100 | 100 | 100 | 100 | 77 |
| $1 \times 10^5$ | 100 | 100 | 100 | 78 | 51 |
| $3 \times 10^4$ | 100 | 100 | 77 | 53 | 24 |
| 0 | 100 | 74 | 52 | 22 | — |

Test Example 5

Application Test in Combination of *D. monoceras* According to the Present Invention and Chemical Herbicide for Broadleaf Weeds 1/1000-are quantitative pots were filled with rice paddy soil, seeded with about 100 seeds per pot of barnyard grass and seeds of broadleaf weeds, i.e., monochoria and narrowleaf water waterplantain, then the plants were grown until the barnyard grass reached the one-leaf stage. The pots were filled with water to a depth of about 5 cm. The plants were treated with the wettable powder prepared according to Formulation Example 1 along with 300 mg of SIRIUS granules (effective component: pyrazosulfron-ethyl). The plants were grown in a weather controlled room (illumination: 10,000 luxes, light/dark: 12/12 hours) set at a temperature of 30° C., then one month after the treatment, the numbers of surviving plants were counted to calculate ratios of controlling barnyard grass by the formula of Test Example 4. The tests were triplicated. Average controlling ratios are shown in Table 5. The controlling ratios for monochoria and narrowleaf waterplantain were both 100% when treated with 300 mg of SIRIUS granules.

TABLE 5

Herbicidal effect of application in combination of
D. monoceras according to the present invention and chemical
herbicide broadleaf plants (average controlling ratio, %)

| Number of conidia | SIRIUS granules (mg) | |
|---|---|---|
| | 300 | 0 |
| $1 \times 10^6$ | 100 | 100 |
| $1 \times 10^5$ | 100 | 76 |
| $1 \times 10^5$ | 100 | 52 |
| $1 \times 10^4$ | 77 | 24 |
| 0 | 13 | — |

*Drechslera monoceras* strains MH-1901, MH-2001 and MH-9011 were respectively deposited on Aug. 29, 1997 and at the National Institute of Bioscience and Human-Technology Agency of Industrial Science and Technology, having an address of 1-3, Higashi 1, chome, Tsukuba-hsi, Ibarakai-ken, 305 in Japan and were respectively accorded Accession Nos. FERM BP-6091, FERM BP-6092 and FERM BP-3416 (May 20, 1991). These deposits were made according to the Budapest Treaty. The strains will be made irrevocably available upon issuance of a patent to this application or any application that claims benefit of priority to this application under 35 U.S.C. §120.

What is claimed is:

1. A strain of *Drechslera monoceras* having selective herbicidal activity against barnyard grass (Echinochloa spp.) at 35° C.

2. The strain of *Drechslera monoceras* according to claim 1 wherein one of the PCR products obtained by a PCR reaction, in which DNA of said *Drechslera monoceras* is used as a template and DNA having a base sequence of SEQ ID NO: 1 is used as a primer, is 1.5 kbp to 1.6 kbp.

3. A conidium of the strain *Drechslera monoceras* according to claim 2.

4. The strain of *Drechslera monoceras* according to claim 1 wherein *D. monoceras* is MH-1901 (FERM BP-6091).

5. A conidium of the strain *Drechslera monoceras* according to claim 4.

6. The strain of *Drechslera monoceras* according to claim 1 wherein *D. monoceras* is MH-2001 (FERM BP-6092).

7. A conidium of the strain *Drechslera monoceras* according to claim 6.

8. A conidium of the strain of *Drechslera monoceras* of claim 1.

9. A conidium of the strain *Drechslera monoceras* according to claim 8.

10. A weed control composition comprising cells of the strain of *Drechslera monoceras* of claim 1 as an effective component and a carrier or a diluent.

11. The weed control composition according to claim 10, which additionally contains one or more chemical herbicides.

12. The weed control composition according to claim 11, wherein said chemical herbicide is one or more herbicides selected from the group consisting of diphenyl ether herbicides, amide herbicides, carbamate herbicides, diazine herbicides, sulfonylurea herbicides and triazine herbicides.

13. The weed control composition according to claim 10 wherein one of the PCR products obtained by PCR reaction, in which DNA of said *Drechslera monoceras* is used as a template and DNA having a base sequence of SEQ ID NO: 1 is used as a primer, is 1.5 kbp to 1.6 kbp.

14. The weed control composition according to claim 13, which additionally contains one or more chemical herbicides.

15. The weed control composition according to claim 10 wherein *D. monoceras* is MH-1901 (FERM BP-6091).

16. The weed control composition according to claim 15, which additionally contains one or more chemical herbicides.

17. The weed control composition according to claim 10 wherein *D. monoceras* is MH-2001 (FERM BP-6092).

18. The weed control composition according to claim 17, which additionally contains one or more chemical herbicides.

* * * * *